US006982284B1

(12) United States Patent
Brown et al.

(10) Patent No.: US 6,982,284 B1
(45) Date of Patent: Jan. 3, 2006

(54) COMPOSITIONS AND METHODS FOR MODIFICATION OF SKIN LIPID CONTENT

(75) Inventors: David A. Brown, Merrick, NY (US); Daniel B. Yarosh, Merrick, NY (US)

(73) Assignee: Applied Genetics Incorporated Dermatics, Freeport, NY (US)

( * ) Notice: Subject to any disclaimer, the term of this patent is extended or adjusted under 35 U.S.C. 154(b) by 218 days.

(21) Appl. No.: 10/070,466

(22) PCT Filed: Sep. 8, 2000

(86) PCT No.: PCT/US00/24659

§ 371 (c)(1),
(2), (4) Date: Mar. 7, 2002

(87) PCT Pub. No.: WO01/17523

PCT Pub. Date: Mar. 15, 2001

Related U.S. Application Data

(60) Provisional application No. 60/153,378, filed on Sep. 10, 1999.

(51) Int. Cl.
*A61K 31/185* (2006.01)
*A61K 31/20* (2006.01)
*A61K 31/56* (2006.01)

(52) U.S. Cl. .................. 514/577; 514/169; 514/560
(58) Field of Classification Search ............... 514/577, 514/169, 560
See application file for complete search history.

(56) References Cited

U.S. PATENT DOCUMENTS

| | | | |
|---|---|---|---|
| 3,903,089 A | 9/1975 | Vanstone | |
| 4,530,934 A | 7/1985 | Clavenna et al. | |
| 4,857,554 A | 8/1989 | Kallimanis | |
| 5,051,449 A | 9/1991 | Kligman | |
| 5,075,340 A | 12/1991 | Barua et al. | |
| 5,147,859 A | 9/1992 | Bombardelli et al. | |
| 5,314,877 A | 5/1994 | Suzuki et al. | |
| 5,556,844 A | 9/1996 | Reichert et al. | |
| 5,624,909 A | 4/1997 | Rao et al. | |
| 5,723,139 A * | 3/1998 | Granger et al. | |
| 5,837,224 A | 11/1998 | Voorhees et al. | |
| RE36,068 E | 1/1999 | Kligman | |
| 6,207,711 B1 | 3/2001 | Matsumoto et al. | |

FOREIGN PATENT DOCUMENTS

| | | |
|---|---|---|
| EP | 1 013 268 | 6/2000 |
| FR | 2 723 313 | 8/1994 |
| JP | 11-5727 | 1/1999 |

OTHER PUBLICATIONS

WPIDS AN 1996-131194, Fontanel et al, FR 2723313, 19960209, abstract.*
CAPLUS 123:208694, Claassen et al, Advances in Space Res. 17(6/7) 1996, 151-60, abstract.*
Abraham et al., 1985, "Linoleate-rich acylglucosylceramides of pig epidermis: structure determination by proton magnetic resonance," *J. Lipid Res.*, 26:761-766.
Baek et al., 1997, "Intracellular $Ca^{2+}$ release mediates ursolic acid-induced apoptosis in human leukemic HL-60 cells," *Int. J. Cancer*, 73:725-728.
Balanehru et al., 1991, "Protective effect of oleanolic acid and ursolic acid against lipid peroxidation," *Biochem. Int.*, 24:981-990.
Bligh et al., 1959, "A rapid method of total lipid extraction and purification," *Canad. J. Biochem. Physiol.*, 37:911-917.
Bonté et al., 1997, "Existence of a lipid gradient in the upper stratum corneum and its possible biological significance," *Arch. Dermatol. Res.*, 289:78-82.
Brincat et al., 1987, "Skin collagen changes in post-menopausal women receiving oestradiol gel," *Maturitas*, 9:1-5.
Cha et al., 1996, "Anti-invasive activity of ursolic acid correlates with the reduced expression of matrix metalloproteinase-9 (MMP-9) in HT1080 human fibrosarcoma cells," *Cancer Res.*, 56:2281-84.
Cha et al., 1998, "Urosolic acid-induced down-regulation of MMP-9 gene is mediated through the nuclear translocation of glucocorticoid receptor in HT1080 human fibrosarcoma cells," *Oncogene*, 16:771-778.
Cox et al., 1986, "Variations in lipids in different layers of procine epidermis," *J. Invest. Dermatol.*, 87:741-744.
Database DRUGU on STN, Derwent Information Ltd., No. 1996-25548, SANG, T. K. "The effect of ursolic acid and all-trans-retinoic acid on ultraviolet A radiation induced elastin mRNA expression in cultured human dermal fibroblast." abstract, *J. Invest. Dermatol.*, 106(4), 836, 1996.
Database DRUGU on STN, Derwent Information Ltd., Kim, S.T. et al. Accession No. 23729, "The effect of all trans-retinoic acid, ursolic acid, ginseng, and aloe extract on ultraviolet A radiation induced collagenase mRNA expression in culture human dermal fibroblast," abstract, *J. Invest. Dermatol.*, 104(4), 621, 1995.
Database DRUGU on STN, Derwent Information Ltd., SEKI, T. et al., Accession 28819. "Effect of Some Alkaloids and Flavonoids and Triterpenoids, Contents of Japanese-Chinese Traditional Herbal Medicines, on the Lipogenesis of Sebaceous Glands," abstract, Sking Pharmacol. 6(1), 56-60, 1993.

(Continued)

Primary Examiner—Rebecca Cook
(74) Attorney, Agent, or Firm—Maurice M. Klee (57) ABSTRACT

The topical use of ursolic acid compounds to alter the lipid content of mammalian skin is disclosed. The compounds can be encapsulated in liposomes and administered in this form to the skin in, for example, a lotion or a gel. The compounds are effective in, among other things, reducing the effects of aging, photoaging, and skin atrophy, including skin atrophy resulting from the topical use of retinoids and/or steroids. Compositions comprising a ursolic acid compound in combination with another therapeutically active topical compounds, such as, a retinoid or a steroid, are also disclosed.

17 Claims, 8 Drawing Sheets

OTHER PUBLICATIONS

Downing et al., "Lipids of the epidermis and the sebaceous glands," *Dermatology in General Medicine*, T. Fitzpatrick et al. editors, McGraw-Hill, New York, 1993, 210-221.

Es-Saady et al., 1996, "MCF-7 cell cycle arrested at G1 through ursolic acid increased reduction of tetrazolium salts," *Anticancer Res.*, 16:481-486.

Es-Saady et al., 1996, "Inhibitory effect of ursolic acid on B16 proliferation through cell cycle arrest," *Cancer Lett.*, 106:193-197.

Farina et al., 1998, "Synthesis and anti-ulcer activity of new derivatives of glycyrrhetic. oleanolic and ursolic acids," *Il Farmaco*, 53:22-32.

Griffiths et al., 1993, "Restoration of collagen formation in photodamaged human skin by tretinoin (retinoic acid)," *New Engl. J. Med.*, 329:530-5.

Griffiths, C. E. M., 1999, "Drug treatment of photoaged skin," *Drugs & Aging*, 14:289-301.

Holleran, et al., 1993, "Processing of Epidermal Glucosylceramides is required for optimal mammalian cutaneous permability barrier function," *Jrnl of Clinical Investiations*, 91:1656-1664.

Holleran et al., 1997, "Structural and biochemical basis for the UVB-induced alterations in epidermal barrier function," *Photoderm. Photoimmunol. Photomed.*, 13:117-128.

Hsu et al., 1997, "Effects of oleanolic acid ursolic acid on inhibiting tumor growth and enhancing the recovery of hematopoietic system postirradiation in mice," *Cancer Lett.*, 111:7-13.

Huang et al., 1994, "Inhibition of skin tumorigenesis by rosemary and its constituents carnosol and ursolic acid," *Cancer Res.*, 54:701-708.

Kennedy et al., 1996, "Stratum corneum lipids of human epidermal keratinocyte air-liquid cultures: implications for barrier function," *Pharmaceut. Res.*, 13:1162-167.

Kligman et al., 1993, "Treatment of photoaged skin with topical tretinoin," *Skin Pharmacol.*, 6(Suppl.1):78-82.

*Liposome Technology*, Gregory Gregoriadis editor, CRC Press Inc., Boca Raton, Florida, 1984, 29-35, 37-49, 68-107.

Liu, J., 1995, "Pharmacology of oleanolic acid and ursolic acid," *J. Ethanopharmacol.*, 49:57-68.

Manez et al., 1997, "Effect of selected triterpenoids on chronic dermal inflammation," *Eur. J. Pharmacol.*, 334:103-105.

Mezzetti et al., 1971, "Chemistry of urosolic acid," *Planta Med.*, 20:244-252.

Najid et al., 1992,"Characterization of ursolic acid as a lipoxygenase and cyclooxygenase inhibitor using macrophages, platelets and differentiated HL60 leukemic cells," *FEBS*, 299:213-217.

Nishimori et al., "A new approach for the improvement of photoaged skin through collagen fiber bundle reconstruction," *Proceedings of the 20th IFSCC Congress*, Cannes, France, Sep. 14-19, 1998, 1-21.

Paik et al., 1998, "Induction of differentiation of the cultured rat mammary epithelial cells by triterpene acids," *Arch. Pharm. Res.*, 21:398-405.

Parker, M., "Design and assessment of preservative systems for cosmetics," *Cosmetic and Drug Preservation. Principles and Practices*, J.J. Kabara editor, Marcel Dekker, New York, 1984, 389-402.

Ponec et al., 1997, "The formation of competent barrier lipids in reconstructed human epidermis requires the presence of Vitamin C," *J. Invest. Dermatol.*, 109:348-355.

Ponec et al., 1990, "Retinoids and lipid changes in keratinocytes," *Meth. Enzymol.*, 190:30-41.

Robert et al., 1999, "Harmful effects of UVA on the structure and barrier function of engineered human cutaneous tissues," *Int. J. Radiat. Biol.*, 75:317-326.

Rogers et al., 1996, "Stratum corneum lipids: the effect of ageing and the seasons," *Arch. Dermatol. Res.*, 288:765-770.

Schaefer H. and Redelmeier, T., 1996, *Skin Barrier: Principles of Percutaneous Absorbption*, Karger, Basel, Switzerland, 1-42.

Suh et al., 1998, "Novel triterpenoids suppress inducible nitric oxide synthase (iNOS) and inducible cyclooxygenase (COX-2) in mouse macrophages," *Cancer Res.*, 58:717-723.

Suh et al., 1999, "A novel synthetic oleanane triterpenoid, 2-cyano-3,12-dioxoolean-1,9-dien-28-oic acid, with potent differentiation, antiproliferative, and anti-inflammatory activity," *Cancer Res.*, 59:336-341.

Swartzendruber et al., 1987, "Evidence that the corneocyte has a chemically bound lipid envelope," *J. Invest. Dermatol.*, 88:709-713.

Tokuda et al., 1986, "Inhibitory effects of ursolic and oleanolic acid on skin tumor promotion by 12-O-tetradecanoyhlphorbol-13-acetate," *Cancer Lett.*, 33:279-285.

Varila et al., 1995, "The effect of topical oestradiol on skin collagen of postmenopausal women," *British Journal of Obstetrics and Gynaecology*, 102:985-989.

Wefers et al., 1991, "Influence of UV irradiation on the composition of human stratum corneaum lipids," *J. Invest. Dermatol.*, 96:959-962.

Ying et al., 1991, "Inhibition of human leucocyte elastase by ursolic acid," *Biochem. J.*, 277:521-526.

FreeTranslation.com's computer-generated English language translation of FR 2 723 313 (Reference 57 above).

WorldLingo.com's computer-generated English language translation of FR 2 723 313 (Reference 57 above).

Database Chemabas Online, Chemical Abstract Service Columbus, Ohio, US; Fedeli et al., "Oleanolic acid activity in topical preparations," XP002285092. CA 104: 95402, 1985.

Patent Abstracts of Japan, vol. 0172 No. 25, May 10, 1993, JP4-360832 (Asahi Chem Ind Co.) Dec. 14, 1992.

Patent Abstracts of Japan, vol. 1997, No. 10, Oct. 31, 1997, JP9-143050 (Pola Chem Ind Inc.) Jun. 3, 1997.

Patent Abstracts of Japan, vol. 1999, No. 03, Mar. 31, 1999, JP10-316555 (Shionogi) Dec. 2, 1998.

Patent Abstracts of Japan, vol. 1999, No. 12, Oct. 29, 1999, JP11-199467 (Nonogawa Shoji KK) Jul. 27, 1999.

Bombardelli, E. "Phytosome: new cosmetic delivery system," *Bollettino Chimico Farmaceutico*, Dec. 1991, vol. 130, No. 11, pp. 431-438.

Le Bang Son et al., Liposomal form of betulinic acid, a selective apoptosis inducing in melanoma cells substance,: *Journal of Liposome Research*, Marcel Dekker, NY, vol. 8, No. 1, Feb. 1998, p. 78.

Suk Kyo Han et al, "Oleanolic acid and ursolic acid stabilize liposomal membranes," *Lipids*, Champaign, IL, vol. 32, No. 7, 1997, pp 769-773.

Yarosh et al., "Liposomal ursolic acid (merotaine) increases ceramides and collagen in human skin," *Hormone Research*, 2000, 54:318-321.

* cited by examiner

FIG. 1A
Untreated

FIG. 1B
1% Empty Liposomes

FIG. 1C
1% 4 mM URA Liposomes

FIG. 1D
1% 4 mM URA Liposomes

COMPOSITIONS AND METHODS FOR MODIFICATION OF SKIN LIPID CONTENT

CROSS REFERENCE TO RELATED APPLICATIONS

This application is the U.S. national phase under 35 USC §371 of International Application No. PCT/US00/24659, filed Sep. 8, 2000, which was published in English under PCT Article 21(2) on Mar. 15, 2001 as International Publication No. WO 01/17523. This application claims the benefit under 35 USC §119(e) of U.S. Provisional Application No. 60/153,378, filed Sep. 10, 1999, the contents of which in its entirety is hereby incorporated by reference.

BACKGROUND OF THE INVENTION

1. Field of the Invention

As known in the art, the epidermis and dermis of mammalian skin contain different cell types, perform different functions, and have different chemical compositions. A particularly important difference between these layers is their lipid concentrations. The dermis contains fibroblasts which produce collagen and other proteins, but very little lipid. The epidermis, on the other hand, contains keratinocytes which, among other things, produce lipids, but essentially no collagen. The collagen produced by the fibroblasts provides tensile strength to the skin. The lipids produced by the kerotinocytes provide a barrier between the living tissue and the outside world.

The present invention relates to modifying the lipid content of skin for purposes of altering appearance, improving function, improving vitality, reversing the effects of aging, reversing the effects of photodamage, or treating disease by topical administration of ursolic acid, ursolic acid analogs, derivatives of ursolic acid, derivatives of ursolic acid analogs, or combinations thereof. Because the skin lipids are located in the epidermis, this modification of the lipid content of the skin takes place in that layer. For ease of reference, ursolic acid, ursolic acid analogs, derivatives of ursolic acid, derivatives of ursolic acid analogs, or combinations thereof will be referred to herein as simply a "ursolic acid compound". The ursolic acid compound can be encapsulated in liposomes or administered in other formulations suitable for topical administration.

2. Description of Related Art

A. Patents

U.S. Pat. No. 4,857,554, Methods for Treatment of Psoriasis, is directed to treating psoriasis by applying an ointment containing ursolic acid and oleanolic acid dispersed in a petroleum jelly/lanolin carrier.

U.S. Pat. No. 4,530,934, Pharmaceutically Active Ursolic Acid Derivatives, is directed to using active derivatives of ursolic acid to treat ulcers.

U.S. Pat. No. 3,903,089, Ursolic Acid Derivatives, is directed to the synthesis of ursolic acid derivatives and analogs.

U.S. Pat. No. 5,624,909, Derivatives of Triterpenoid Acids as Inhibitors of Cell-adhesion Molecules ELAM-1 (e-selectin) and LECAM-1 (I-selectin), is directed to alleviating inflammation by administration of triterpenoid acid derivatives.

U.S. Pat. No. 5,314,877, Water-soluble Pentacyclic Triterpene Composition and Method for Producing the Same, is directed to making ursolic acid, oleanolic acid, and related triterpenoids soluble in water by formulation in cyclodextrins.

U.S. Reissue Patent RE036068, Methods for Treatment of Sundamaged Human Skin with Retinoids, is directed to reversing the effects of photodamage by topical application of retinoids.

U.S. Pat. No. 5,051,449, Treatment of Cellulite with Retinoids, is directed towards retarding or reversing cellulite accumulation in skin by topical application of retinoids.

U.S. Pat. No. 5,556,844, Pharmaceutical or Cosmetic Composition Containing a Combination of a Retinoid and a Sterol, is directed towards treatment of disorders of epidermial keratinization, epithelial proliferation, or disorders of sebaceous function by topical application of retinoids.

U.S. Pat. No. 5,075,340, Retinoic Acid Glucuronide Preparations for Application to the Skin, is directed towards treatment of acne or wrinkled skin and prevention of retinoid dermatitis by topical application of retinoic acid glucoronides.

U.S. Pat. No. 5,837,224, Method of Inhibiting Photoaging of Skin, is directed to reversing the effects of photodamage by topical application of agents that inhibit UVB-inducible matrix metalloproteinase.

B. Publications

Tokuda, H., H. Ohigashi, K. Koshimizu, and Y. Ito. 1986. Inhibitory effects of ursolic and oleanolic acid on skin tumor promotion by 12-O-tetradecanoyhlphorbol-13-acetate. Cancer Lett. 33:279–285.

Ponec, M., and A. Weerheim. 1990. Retinoids and lipid changes in keratinocytes. Meth. Enzymol. 190:30–41.

Griffiths, C. E. M., A. N. Russman, G. Majmudar, R. S. Singer, T. A. Hamilton, and J. J. Voorhees. 1993. Restoration of collagen formation in photodamaged human skin by tretinoin (retinoic acid). New Engl. J. Med. 329:530–5.

Kligman, A. M., and J. J. Leyden. 1993. Treatment of photoaged skin with topical tretinoin. Skin Pharmacol. 6 (Suppl.1):78–82).

Huang, M.-T., C.-T. Ho, Z. Y. Wang, T. Ferraro, Y.-R. Lou, K. Stauber, W. Ma, C. Georgiadis, J. D. Laskin, and A. H. Conney. 1994. Inhibition of skin tumorigenesis by rosemary and its constituents carnosol and ursolic acid. Cancer Res. 54:701–708.

Liu, J. 1995. Pharmacology of oleanolic acid and ursolic acid. J. Ethanopharmacol. 49:57–68.

Manez, S., C., C. Recio, R. M. Giner, and J.-L. Rios. 1997. Effect of selected triterpenoids on chronic dermal inflammation. Eur. J. Pharmacol. 334:103–105.

Ponec, M., A. Weerheim, J. Kempenaar, A. Mulder, G. S. Gooris, J. Bouwstra, and A. M. Mommaas. 1997. The formation of competent barrier lipids in reconstructed human epidermis requires the presence of Vitamin C. J. Invest. Dermatol. 109:348–355.

Griffiths, C. E. M. 1999. Drug treatment of photoaged skin. Drugs & Aging 14:289–301.

Japanese Patent Publication No. 11–5727, published Jan. 12, 1999, describes the use of ursolic acid in combination with retinols in a final cosmetic product to increase dermal collagen. As discussed above, collagen is located and produced in the dermis by fibroblasts. The present invention, on the other hand, is concerned with modifying the content of lipids located and produced in the epidermis by kerotinocytes.

3. Epidermal Livid Composition and Alterations During Differentiation

The epidermis of skin contains a number of lipids that are altered during differentiation as follows (see Downing et al., 1993, p210–221, In: Dermatology in General Medicine):

(i) Phospholipids: Most common are phosphatidylcholine, phosphatidylethanolamine, phosphatidylserine, phosphatidylinositol, and sphingomyelin. Phospholipids are the most abundant lipids in the basal layers of the epidermis, but decrease towards the surface of the skin so much so that they are one of the least abundant lipids in the cornified layer. Thus, the phospholipid content of keratinocytes decreases as they differentiate. Conversely, high phospholipid levels are associated with keratinocyte proliferation.

(ii) Free fatty acids: These are primarily saturated and range from 14 to 28 carbons (myristic=14, palmitic=16, stearic=18, arachidic=20, behenic=22, lignoceric=24, cerotic=26). The most common fatty acids in skin are the 22-carbon (15 wt. %) and 24 carbon (27 wt. %) species.

(iii) Triglycerides: These are minor lipid components that serve as intermediates in the transfer of fatty acids from phospholipids to glucosylceramides.

(iv) Glucosylceramides A,B,C-1,C-3,D-1,D-2, C-2: Glucosylceramide A also known as acylglucosylceramide is the major form, comprising 56 wt. % of this group of lipids. The acyl group in glucosylceramide A is often linoleic acid which is bound to the hydroxyl group of the ω-hydroxyacid (Abraham, Wertz and Downing, 1985, J. Lipid Res. 26:761–766).

(v) Ceramides 1–7: Ceramides are the major lipids in the stratum corneum. They result from deglycosylation of glucosylceramides at the end of the epidermal differentiation process. Ceramide 1 is derived from Glucosylceramide A, Ceramide 2 is derived from Glucosylceramide B, Ceramide 3 is derived from Glucosylceramide C-1, Ceramide 4 is derived from Glucosylceramide C-3, Ceramide 5 is derived from Glucosylceramide D-1, Ceramide 6-A is derived from Glucosylceramide D-2, and Ceramide 6-B is derived from Glucosylceramide C-2. Although Glucosylceramide A comprises 56 wt. % of the glucosyleramides, Ceramide 1 comprises only 8 wt. % of the extractable ceramides because most of it is converted to the (ω-hydroxyceramide which permits covalent binding to glutamates of the cornified cell envelope protein, thus, forming a protective barrier around each corneocyte. Ceramide 2 comprises 42 wt. % of this group. Ceramide 6 (phytosphingosine) and ceramide 7 (6-hydroxy-4-sphingenine) together comprise 20 wt. %.

(vi) Cholesterol: This lipid increases as keratinocytes differentiate so that it comprises 30 mol % of stratum corneum lipids (Schaefer and Redelmeier, 1996, Skin Barrier).

(vii) Cholesterol sulfate: This lipid increases cell cohesiveness by forming intercellular cholesterol sulfate calcium bridges.

(viii) Cholesterol esters: During the latter stages of epidermal differentiation, phospholipids are degraded liberating fatty acids which are utilized to produce cholesterol esters.

Examination of lipids in serial sections through pig skin showed the following (Cox and Squier, 1986, J. Invest. Dermatol. 87:741–744): (i) increases of both glucosylceramides and ceramides towards the surface layers, but decreases of glucosylceramides concomitant with increases of ceramides at the outermost layers, (ii) decreases of phospholipids towards the surface layers of the skin (iii) progressive increases of triglycerides, cholesterol and cholesterol esters towards the surface layers of the skin, (iv) progressive increase of cholesterol sulfate and then a sudden decrease at the outermost layer (related to desquamation by a sulfatase).

Ponec and Weerheim (1990, Meth. Enzymol. 190:30–41) reviewed the literature and state that normal epidermal terminal differentiation is marked by depletion of phospholipids, with increase of sterols and certain classes of sphingolipids, with the final stratum corneum lipid products of differentiation consisting mainly of ceramides and nonpolar lipids. Overall, the flow of fatty acids during differentiation appears to be from phospholipids, to triglycerides, to ceramides, and finally hydroxy-ceramides (Swartzendruber et al., 1987, J. Invest. Dermatol. 88:709–713; Ponec et al., 1997, J. Invest. Dermatol. 109:348–355). Thus the metabolic lipid flow during differentiation appears to be towards formation of hydroxy-ceramides in the stratum corneum. Hydroxyceramides are linked to involucrin via its numerous glutamate residues (20%) during cornification, resulting in the highly effective barrier function of the skin (Swartzendruber et al., 1987, J. Invest. Dermatol. 88:709–713).

4. Agents Shown to Alter Epidermal Lipids

Retinoic acid is able to reverse the alterations of lipid synthesis that occur during differentiation, resulting in a 3–4-fold increase in phospholipids, a 3-fold decrease in sphingolipids (most notably, ceramides), a 9-fold decrease of acylceramides, a near 2-fold decrease of cholesterol and cholesterol sulfate, a 6-fold decrease of lanosterol, and a 3-fold decrease of FFA in living skin equivalents (Ponec and Weerheim, 1990, Meth. Enzymol. 190:30–41). Thus, it would appear that there are marked differences between the terminal differentiation that occurs naturally in skin, and the cellular reprogramming that occurs as a result of treatment with retinoic acid.

Vitamin C (50 ug/ml) has been found to result in increases of glucosylceramides and ceramides, most notably ceramides 6 and 7 in living skin equivalents (Ponec et al., 1997, J. Invest. Dermatol. 109:348–355). These increases were accompanied by increased barrier function. Since Vitamin E had no effect on lipid composition even though it is hydrophobic, it was concluded that the main role of Vitamin C is as a donor of hydroxyl groups to sphingoid bases and fatty acids for the formation of protein-bound hydroxyceramides (Ponec et al., 1997, J. Invest. Dermatol. 109:348–355).

5. Effect of Aging on Epidermal Lipids

All major species of epidermal lipids are decreased during the aging process. Particular attention has been paid to the reductions of the ceramide fraction since this results in a notable loss of barrier function with age (reviewed in Rogers et al., 1996, Arch. Dermatol. Res. 288:765–770). However, the percentage ratio of each of the major classes of lipids is unchanged during aging, even though total epidermal lipids are decreased by 30% in the aged (Rogers et al., 1996, Arch. Dermatol. Res. 288:765–770). The most important change of epidermal lipids that occurs with age is related to altered ratios of free fatty acids that result in reductions in ceramide 1 lineolate (Rogers et al., 1996, Arch. Dermatol. Res. 288:765–770). Reductions of ceramide 1 lineolate have been linked to dry skin, atopic dermatitis, and acne (reviewed in Rogers et al., 1996, Arch. Dermatol. Res. 288:765–770).

6. Effect of Photodamage on Epidermal Lipids

Long-term (3 week) daily treatment with either UVA (50 J/cm$^2$) or UVB (124 mJ/cm$^2$) has been shown to result in an approximate 2-fold increase of total epidermal lipids in human skin, with increases in the triglyceride, free fatty acid, alkane, squalene, and ceramide fractions (Wefers et al.

1991, J. Invest. Dermatol. 96:959–962). No changes were found in the sterol, cholesterol, cholesterol ester or cholesterol sulfate fractions (Wefers et al., 1991, J. Invest. Dermatol. 96:959–962). Phospholipids were not examined in this study. In contrast to these results, shortly after exposure (24–48 hr), UVA (50 J/cm$^2$) resulted in a decrease of the ceramide fraction of living skin and an increase in the relative proportion of phospholipids (Robert et al., 1999, Int. J. Radiat. Biol. 75:317–26). Similarly, shortly after exposure (24–48 hrs), UV-B (0.15 J/cm$^2$) resulted in a marked depletion of ceramides (Holleran et al., 1997, Photoderm. Photoimmunol. Photomed. 13:117–128). However, unlike UV-A, short-term exposure to UV-B also resulted in a marked (>2-fold) depletion of phospholipids (Holleran et al, 1997, above).

7. Methods to Treat Aged and Photodamaged Skin

Retinoic acid is well known as an agent for treatment of photoaged skin. Topical retinoic acid has been shown to restore collagen I levels that are reduced in photodamaged skin (Griffiths et al., 1993, New Engl. J. Med. 329:530–5). Restoration of collagen I levels correlate with a reduction of fine wrinkles in skin (Griffiths et al., 1993, New Engl. J. Med. 329:530–5). Although retinoids have been shown to alter lipids in cultured skin equivalents (Ponec and Weerheim, 1990, Meth. Enzymol. 190:30–41), there are no reports indicating that retinoids reverse aging or photodamage by altering lipid levels. In part, this may be because retinoids reduce ceramide levels in skin equivalents (Ponec and Weerheim, 1990, Meth. Enzymol. 190:30–41), and reduce the thickness of the stratum corneum when applied topically to human skin (Kligman and Leyden, 1993, Skin Pharmacol. 6, Suppl.1:78–82), which could exacerbate the depletion of ceramides and barrier function that occurs in the aged.

8. Pharmacological Uses of Ursolic Acid

Ursolic acid is pentacyclic triterpene compound known to have a number of pharmacological effects (reviewed in Liu, 1995, J. Ethanopharmacol. 49:57–68). Ursolic acid is closely related to steroids since both are derived from the cyclization of squalene (Suh et al., 1998, Cancer Res. 58:717–723). It is found in the waxy coating of fruit and in the leaves of many plants, such as heather and rosemary. It is insoluble in most common solvents and as a result it is not widely used. In fact, commercial extraction processes for plant leaves fail to recover measurable levels of ursolic acid.

Ursolic acid has been characterized as an inhibitor of lipoxygenase and cyclooxygenase in inflammatory cells (Najid et al., 1992, FEBS 299:213–217; Suh et al., 1998, Cancer Res. 58:717–723). As such, ursolic acid is expected to have usefulness as an anti-inflammatory agent. Ursolic acid has been shown to inhibit chronic dermal inflammation induced by phorbal esters in an animal model (Manez et al., 1997, Eur. J. Pharmacol. 334:103–105). Ursolic acid has also been shown to inhibit induction of inducible nitric oxide synthase in macrophages (Suh et al., 1998, Cancer Res. 58:717–723), which may contribute to its anti-inflammatory activity.

Ursolic acid has also been shown to induce differentiation and growth arrest of several types of cells, suggesting that it may be useful as a chemotherapeutic differentiation agent (Es-Saady et al., 1996, Cancer Lett. 106:193–197; Hsu et al., 1997, Cancer Lett. 111:7–13; Es-Saady et al., 1996, Anticancer Res. 16:481–486; Paik et al., 1998, Arch. Pharm. Res. 21:398–405). Ursolic acid has also been shown to induce apoptosis in tumor cells (Baek et al., 1997, Int. J. Cancer 73:725–728). Both ursolic acid and oleanolic acid, a closely related structural analog of ursolic acid, have been shown to inhibit tumor promotion induced in mouse skin by phorbal esters Tokuda et al., 1986, Cancer Lett. 33:279–285; Huang et al., 1994, Cancer Res. 54:701–708). Both compounds have also been shown to prevent lipid peroxidation, which may inhibit free radical damage during cancer initiation and promotion (Balanehru and Nagarajan, 1991, Biochem. Int. 24:981–990).

Ursolic acid also downregulates matrix metalloproteinases (Cha et al., 1998, Oncogene 16:771–778) and elastase (Ying et al., 1991, Biochem. J. 277:521–526) which may provide a mechanism for preventing tumor invasion (Cha et al., 1996, Cancer Res. 56:2281–84), and, inflammation related damage in skin (Ying et al., 1991, Biochem. J. 277:521–526).

Ursolic acid and a number of triterpenoid derivatives have been shown to have hypolipidemic and anti-atherosclerotic properties (reviewed in Liu, 1995, J. Ethanopharmacol. 49:57–68). Ursolic acid and oleanolic acid lowered blood cholesterol and β-lipoprotein levels 40–50% in animal models of atherosclerosis (reviewed in Liu, 1995, J. Ethanopharmacol. 49:57–68). Consistent with this prior art understanding, topical ursolic acid has been proposed for use in the treatment of psoriasis, a condition characterized by hyperproliferation and inflammation of the epidermis (U.S. Pat. No. 4,857,554). In fact, these prior results that ursolic acid and its analogs decrease lipid production and may be used in treatment of the hyperproliferation of psoriasis teach away from the present invention, and make the discovery of the opposite effects unexpected and novel. Contrary to the findings in the literature and the understanding of the prior art, we have discovered that ursolic acid increases the production of lipids, especially ceramides and phospholipids, by keratinocytes of the skin.

SUMMARY OF THE INVENTION

The present invention provides a method for altering the lipid content of mammalian skin by administering an effective amount of a ursolic acid compound to the skin of a mammal (e.g., a human) in need of such a treatment, e.g., to skin which is aged, photoaged, atrophied, etc. As discussed above, because the lipids of the skin are located in the epidermal layer, the alteration of the lipid content of the skin takes place in that layer.

In another aspect, the present invention provides a method for reversing certain aspects of the photoaging or aging process in mammalian skin and, in yet another aspect, the present invention provides a method for improving function, increasing barrier function, improving vitality, or treating lipid deficient diseases of mammalian skin, which comprises topical application of:

(a) an effective amount of a ursolic acid compound in a suitable medium for topical administration, e.g., a lotion, gel, or the like;

(b) an effective amount of a ursolic acid compound encapsulated in liposomes; and/or (c) an effective amount of a ursolic acid compound encapsulated in liposomes and incorporated into a suitable medium for topical administration, e.g., a lotion, gel, or the like.

As discussed below, because ursolic acid compounds are highly insoluble in many solvents, including water, administration of such compounds in liposomes is a particularly preferred embodiment of the invention.

DETAILED DESCRIPTION OF THE INVENTION

The compounds and compositions of the present invention effectively and efficiently increase the phospholipid content of normal human epidermal keratinocytes. Furthermore, the compounds and compositions of the present invention increase the free fatty acid content and the ceramide and glycosylceramide content of normal human epidermal keratinocytes. Increases of phospholipid, free fatty acid, ceramide and glycosylceramide content are due to the effects of ursolic acid and are over and above any effects of the lipid carrier.

Increasing the lipid content of epidermal keratinocytes has several consequences. First, increasing the phospholipid content prevents cell senescence and stimulates proliferation, which is manifested as increased cellular viability and increased epidermal thickening. Second, increasing the free fatty acid content relates to increases of several lipid fractions including phospholipids, triglycerides, glucoceramides, ceramides and acylceramides. Increasing the lipid content of epidermal keratinocytes reverses the lipid reductions associated with aging. Third, increasing the glucoceramide, ceramide and acylceramide content of keratinocytes results in an improved barrier function. Improved barrier function, in turn, reduces atopic dermatitis and protects the skin and body from the effects of many agents including ultraviolet irradiation, toxic chemicals, toxins, and irritants. Fourth, preventing cell senescence and increasing barrier function reverses the effects of aging. Fifth, increases of phospholipids directly reverse the depleting effect of UV-B on phospholipids in skin, resulting in increased viability as manifested by cellular proliferation, and reducing the effects of photoaging.

The users of this invention who benefit from its discovery include, among others, those suffering from ichthyosis and ichthyosiform dermatoses, those with acute dry skin, those with skin atrophy and retinoid dermatoses, those with acne and those with aging and photoaging skin. These conditions all have in common a reduction of skin lipids, particularly those produced by keratinocytes and especially ceramides, a reduction in the thickness and uniformity of intact stratum corneum and a loss of skin barrier function. As a consequence, the users of this invention share the pathological conditions of increased transepidermal water loss and a sensation of dry skin.

The active compound according to the present invention is a ursolic acid compound. Examples of such compounds are set forth in Table 1, it being understood that the invention is not limited to the examples of this table but includes all ursolic acid compounds which achieve the beneficial, lipid altering effects of the invention when applied to mammalian skin.

The table shows the chemical structure common to this family of compounds. The reference compound, ursolic acid, contains the substituents at the indicated sites as shown in the second line of the table. Each of the analogs/derivatives listed below ursolic acid differs from the ursolic acid structure only where indicated. Blank cells indicate that the substituents at those sites are identical to ursolic acid. As can be appreciated from the diagram, these compounds share great similarity in the A, B, and C rings of the pentacyclic structure. An addition at sites on any of these rings, such as the hemisuccinate at the $R_2$ position of ring A in carbenoxolone, reduces the potency of the compound despite the increase in solubility that may be achieved by the addition. On the other hand, many modifications of the E ring, including larger alkyl groups at the $R_6$ position and substitution of a pentyl for a hexyl ring, can be tolerated. Oxo additions at the $R_4$ position increase the mineralocorticoid activity of the compound and are to be preferred only when anti-diuresis and water retention is desirable or not harmful.

As discussed above, the methods and compositions of the present invention employ a ursolic acid compound (which, as defined above, can be a combination (mixture) of compounds) as an active ingredient for various uses. In a preferred embodiment, the active ingredient is given topically in an acceptable formulation. A particularly preferred formulation is the incorporation of the ursolic acid compound into liposomes. A variety of different types of lipids at various concentrations can be used to form the liposomes, examples of which can be found in Liposome Technology, ed. Gregory Gregoriadis, CRC Press Inc., Boca Raton, Fla. 1984. The present invention also relates to the incorporation of the ursolic acid compound, either alone or incorporated in liposomes, into lotions, gels, creams or other acceptable formulations conducive to uptake of active ingredients into the epidermis.

Liposomal formulations are preferred because ursolic acid is highly insoluble in many solvents, particularly water, and common emulsifiers such as LECINOL S-10 have little effect. In accordance with the invention, this insolubility problem is addressed by taking advantage of the flat, planar structure of ursolic acid to stack it between the lipid tails in the phospholipid bilayer membranes of liposomes. Due to the charged headgroup of the phospholipids, liposomes containing ursolic acid are readily soluble in water.

However, only a limited number of sites within the tails of the lipid bilayer of the liposome membrane are available for stacking ursolic acid. The preferred ratio of ursolic acid to lipid components must be determined by experimentation. For example, the preferred ratio of ursolic acid to phosphatidylcholine and cholesterol is approximately 1.5 (range 1.0 to 3.0):10:1.9 (w/v). At lower concentrations of ursolic acid, the effects on lipid production by the epidermal layer of mammalian skin are not easily evoked. At the higher ranges of ursolic acid concentration, other compounds that partition into the liposome membrane cannot be included in the preparation, because they displace the ursolic acid and lead to its precipitation.

For example, inclusion of the lipophilic preservative phenoxyethanol at the recommended concentration of 1% leads to a ursolic acid precipitate forming in the preparation. Therefore it is difficult to achieve an effective concentration of ursolic acid in liposomes and an effective concentration of a lipophilic preservative. The preferred preservatives that are compatible with ursolic acid liposomes are water-soluble preservatives that do not partition into the liposome membrane. One such water-soluble preservative that can be used in the practice of the invention is potassium sorbate. Other water soluble preservatives can be found in: Cosmetic and Drug Preservation. Principles and Practices. Ed. J. J. Kabara. Marcel Dekker, Inc. New York, 1984.

Similarly, other additives to a liposomal ursolic acid composition should not displace the ursolic acid from the liposome, and the preferred form of such additives should be water soluble or otherwise sequestered from the liposomes.

The dose regimen will depend on a number of factors which may be readily determined, such as severity and responsiveness of the condition to be treated, but will normally be one or more treatments per day, with treatment lasting from several days to several months, or until the desired response is obtained, or a cure is effected, or a remediation of a condition or a diminution of a disease state is achieved. One of ordinary skill may readily determine optimum dosages, dosing methodologies and repetition rates. In general, the unit dosage for compositions according to the present invention will contain from 0.1 mM to 10 mM of the ursolic acid compound in liposomes or an alternative carrier, with said liposomes or carrier comprising from 1 wt. % to 90 wt. % of a lotion or alternative topical formulation. In some instances, it may be preferable to apply said liposomes or alternative formulations full strength to skin.

If desired, the ursolic acid compound can be combined with other active ingredients in the formulation. For example, it is known that retinoids and topical steroids have the undesirable side effect of skin atrophy. This side effect can be ameliorated by co-administration of a ursolic acid compound with these agents. The co-administration can be performed using a single vehicle, e.g., a lotion, containing both active ingredients or by means of separate vehicles, e.g., separate lotions, which can be administered either simultaneously or sequentially, with either agent being administered first. As another example, a ursolic acid compound can be combined with a sunblock to form a sunscreen product.

The uses of and useful and novel features of the present methods and compositions will be further understood in view of the following nonlimiting examples.

EXAMPLE 1

Preparation of Liposomes

Ursolic acid-containing liposomes and empty liposomes containing no ursolic acid were prepared as follows: 0.393 g phosphatidylcholine (DOOSAN) and 0.077 g cholesterol (AVANTI) were dissolved in 20 ml ethanol, and split into two 10 ml aliquots. Sixty mg ursolic acid (SIGMA-ALDRICH) was then dissolved in one aliquot which was then used to make Ursolic Acid Liposomes. No additions were made to the aliquot designated as Empty Liposomes. Seven ml of each mixture were injected through a 30½ G needle into 10 ml cold 1XPBS. The resulting mixture was dialyzed for 2 hr in 2 liters 1XPBS, and then overnight in a fresh batch of 1XPBS. Liposomes were collected and ursolic acid content was measured by high performance thin layer chromatography (HPTLC) using RP-18 $F_{254}S$ HPTLC plates (MERCK). Ursolic acid was dissolved in methanol to make a series of standards. Liposomes were applied directly to HPTLC plates. The mobile phase was 100% methanol. Chromatograms were visualized by spraying with antimony trichloride followed by heating at 100° C. for 5 min. Stained chromatograms were photographed and spots were analyzed by QUANTISCAN image analysis software. Ursolic Acid Liposomes contained 4 mM ursolic acid.

Cell Culture and Treatments

Normal human epidermal keratinocytes (NHEK) were obtained from CLONETICS BIOWHITTAKER and cultured in KGM-2 media (CLONETICS-BIOWHITTAKER) according to the manufacturer's instructions. Four days before beginning treatments, $10^5$ NHEK were plated in each of six 10 $cm^2$ CORNING cell culture dishes in 10 ml KGM-2 media. Two days later and on the first day of treatments, media was replaced with 10 ml fresh media.

On the first day of treatments, 100 ul Empty Liposomes were added to each of two dishes, and 100 ul 4 mM Ursolic Acid Liposomes were added to each of two dishes. Thus, the Empty Liposome and 4 mM Ursolic Acid Liposome treatments each received 1% liposomes, and the final concentration of ursolic acid in the Ursolic Acid Liposome treatment was 40 uM. All treatments received fresh media and liposomes on the fourth day following the initiation of treatments.

Cells were harvested 8 days following the initiation of treatments. Media was removed and cells were washed once with 10 ml CLONETICS-BIOWHITTAKER Hank's Buffered Saline Solution (HBSS), then 5 ml HBSS was added, and cells were photographed using a NIKON microscope equipped with camera linked to a NORTHERN EXPOSURE computer imaging system. Following photograph, HBSS was removed, 6 ml CLONETICS Trypsin/EDTA was added, and cells were incubated at 37° C. for 6 min until they detached from dishes. Then, 6 ml CLONETICS Trypsin Neutralization Solution was added, and the cells were mixed thoroughly and transferred to a 15 ml conical tube. One-half ml of suspended cells were added to 19.5 ml Isoton II and counted on a model ZBI COULTER counter. The remainder of cells were then pelleted by centrifugation at 178×g for 5 min. Supernatant was removed and cells were then resuspended in 5 ml 1XPBS, transferred to a PYREX test tube with teflon-lined lid, and pelleted for lipid extraction.

Lipid Extraction Method

Lipids were extracted using procedures developed by Ponec and Weerheim (1990, Meth. Enzymol. 190:30–41), that were a modification of procedures developed by Bligh and Dyer (1959, Canad. J. Biochem. Physiol. 37:911–917). Pelleted cells were extracted by mixing with 2 ml chlorform:methanol (2:1) for 60 min at room temperature (RT) on a LABQUAKE rotary mixer. Cellular debris was pelleted, the supernatant collected, and the pellet re-extracted with 2 ml chloroform:methanol:deionized water (1:2:0.5) for 60 min at 37° C., followed by 2 ml chloroform:methanol (1:2) for 30 min at RT, 2 ml chloroform:methanol (2:1) for 30 min at RT, and 2 ml chloroform at for 15 min at RT. The combined extracts were mixed with 200 ul 2.5% KCl by vortexing, and then mixed with 2 ml deionized water for 10 min at RT. Both the upper aqueous layer and the bottom extract layer were transferred to clean tubes, and the aqueous layer was re-extracted with 4 ml chloroform by mixing for 10 min at RT. This chloroform extract was combined with the previous extracts. The combined extracts were placed in a 50° C. water bath and dried under a stream of nitrogen. The pellet was dissolved in 500 ul chloroform(2):methanol(1) and stored in a teflon lined vial under nitrogen at −20° C.

For analysis of lipids in human skin, lipids were extracted from subjects using a modification of the protocol described by Bonté, F., A. Saunois, P. Pinguet, and A. Meybeck, in Arch. Dermatol. Res. 289:78–82, 1997. Following treatments, the area on the forearm to be extracted was first rinsed with tap water, dried thoroughly and then tape-stripped once with SCOTCH™ 810 MAGIC™ tape. The excised top 1-inch of 50 ml polypropylene conical tubes were used as reservoirs for the solvents during extraction of subjects. The reservoirs were placed and held firmly on the arm and 1 ml of cyclohexane:ethanol (4:1) was added and stirred gently for one minute. Solvent was then removed and placed into a pyrex tube with a teflon-lined lid. One ml of cyclohexane:ethanol (1:1) was then added to the reservoir, stirred for one minute, and then removed and added to the tube containing the first extract. The tubes were then dried at 50° C. under nitrogen gas as described above. The dried extracts were dissolved in 200 $\mu$l of chloroform:methanol (2:1). The lipid solution was then placed into a small storage tube with a teflon-lined lid, purged with nitrogen gas and stored at −20° C.

Thin Layer Chromatography Methods

Standard solutions were prepared that contained 5 ug/ul each of phosphatidylcholine (PC), phosphatidylethanolamine (PE), cholesterol (CH), total ceramides ($\alpha$-hydroxy ceramides+non-hydroxy ceramides)(Cer), total glycosylceramides (GlyCer), and oleic acid, a commonly used reference material for free fatty acids (FFA). These were then serially diluted to 2.5 ug/ul, 1.25 ug/ul, 0.625 ug/ul, 0.313 ug/ul, 156 ng/ul, and 78 ng/ul, and 5 ul of each were run on 250 um thick Silica TLC plates with polyester support (SIGMA-ALDRICH) for PC and PE, or, on 150 um thick Silica HPTLC plates with glass support (SIGMA-ALDRICH) for FFA, CH, Cer, and GlyCer. TLC plates were developed by running chloroform:methanol:deionized water (65:30:5) 60 mm as the mobile phase. HPTLC plates were developed using the following sequence of mobile phases for FFA and CH: (i) chloroform run 15 mm, (ii) chloroform-acetone-methanol (76:8:16) run 10 mm, (iii) chloroform-hexyl acetate-acetone-methanol (86:1:10:4) run 70 mm, (iv) chloroform-acetone-methanol (76:4:20) run 20 mm, (v) chloroform-diethyl ether-hexyl acetate-ethyl acetate-acetone-methanol (72:4:1:4:16:4) run 75 mm, and, (vi) hexane-diethyl ether-ethyl acetate (80:16:4) run 90 mm (Ponec and Weerheim, 1990, Meth. Enzymol. 190:30–41), or, the following sequence of mobile phases for Cer and GlyCer: (i) chloroform-methanol-water (40:10:1) run 30 mm, (ii) chloroform-methanol-glacial acetic acid (190:9:1) run 75 mm, (iii) hexane-diethyl ether-glacial acetic acid (80:20:10) run 75 mm, and (iv) petroleum ether run 85 mm (Kennedy et al., 1996, Pharmaceut. Res. 13:1162–1167). TLC plates were dried, stained with iodine, photographed, and analyzed using a QUANTASCAN computer imaging system. HPTLC plates were dried, sprayed with phosphomolybdic acid, baked at 120° C. for 2 min for FFA and CH, or, sprayed with 10% copper sulfate in 8% phosphoric acid for Cer and GlyCer, and analyzed similar to TLC plates. Intensity of standard staining was found to be linear up to at least 0.625 ug/ul, and this was therefore used as a standard on chromatographic runs with samples.

Samples were run using either a standard amount of extract (5 ul), followed by normalization of results to cell number, or by loading an amount of extract equivalent to a standard number of cells ($2.5 \times 10^4$ cells). Both techniques produced similar results. Results obtained using extracts from a standard number of cells are shown in this example. TLC's and HPTLC's were run, stained and quantified in a fashion identical to that described above for standards. Statistical analysis was done by Student-Newman-Keuls ANOVA using the INSTAT software.

Results and Pharmacological Applications

Visual observation and photographic record (FIG. 1) showed NHEK cells treated with 1% 4 mM Ursolic Acid Liposomes were highly vacuolated relative to Untreated cells or cells treated with Empty Liposomes. Vacuolation can result from several conditions including accumulation of lipid (Robert et al., 1999, Int. J. Radiat. Biol. 75:317–326). In light of the lipid analysis below, it is believed that the vacuoles observed here resulted from lipid accumulation. It should be noted that there was little or no increase in vacuolation of NHEK treated with Empty Liposomes, despite the fact that liposomes contain phosphatidlycholine and cholesterol. Thus, the vacuolation observed here is specific for Ursolic Acid Liposome treated cells, indicating that ursolic acid is responsible for induction of vacuolation. Although the photographs in FIG. 1 were taken after 8 days of treatment, visual observation indicated that significant vacuolation of Ursolic Acid Liposome treated cells was apparent as soon as 2 days after the initiation of treatments.

Figure 1A:
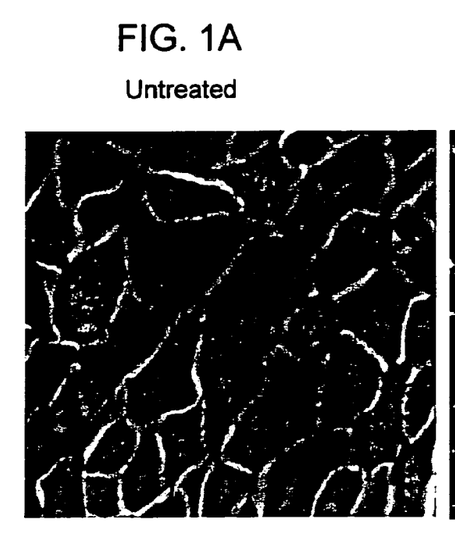
FIG. 1 shows micrographs of cultured normal human epidermal keratinocytes (NHEK) that were: (a) Untreated, (b) treated with 1% (volume/volume) Empty Liposomes, (c & d) treated with 1% 4 mM Ursolic Acid (URA) Liposomes, which are identical to Empty Liposomes except for incorporation of ursolic acid at a concentration of 4 mM—the final concentration of ursolic acid in media is 40 uM. Details are described in Example 1.
Figure 1B:
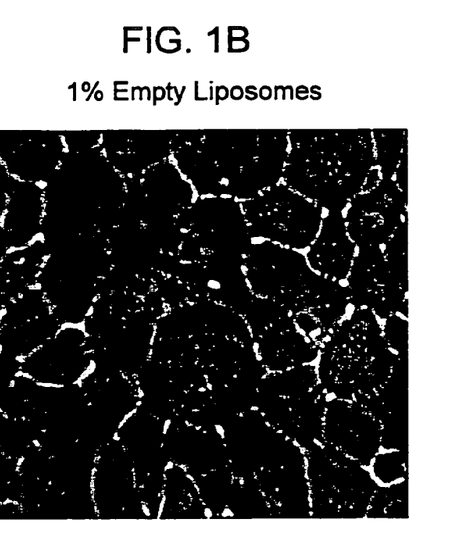
Figure 1C:
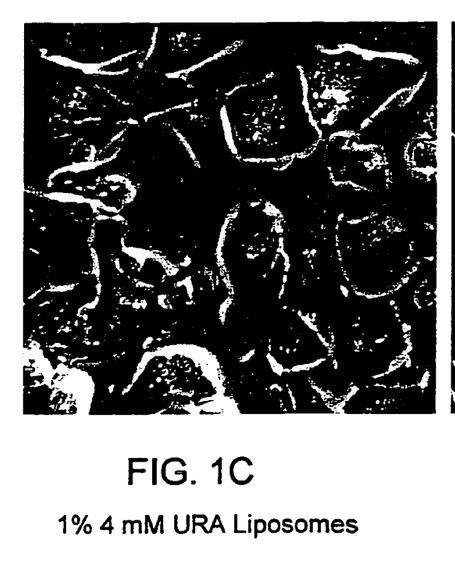
Figure 1D:
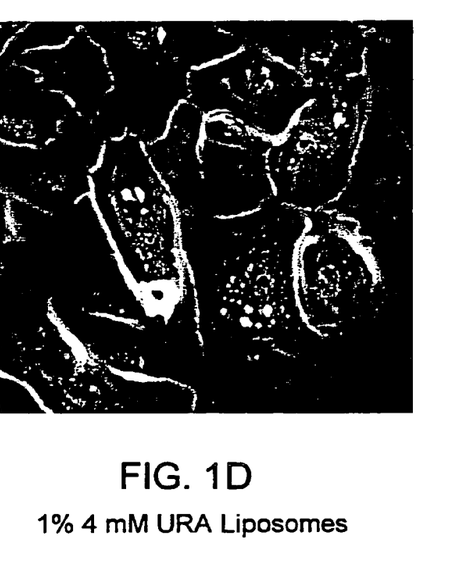
Figure 2:
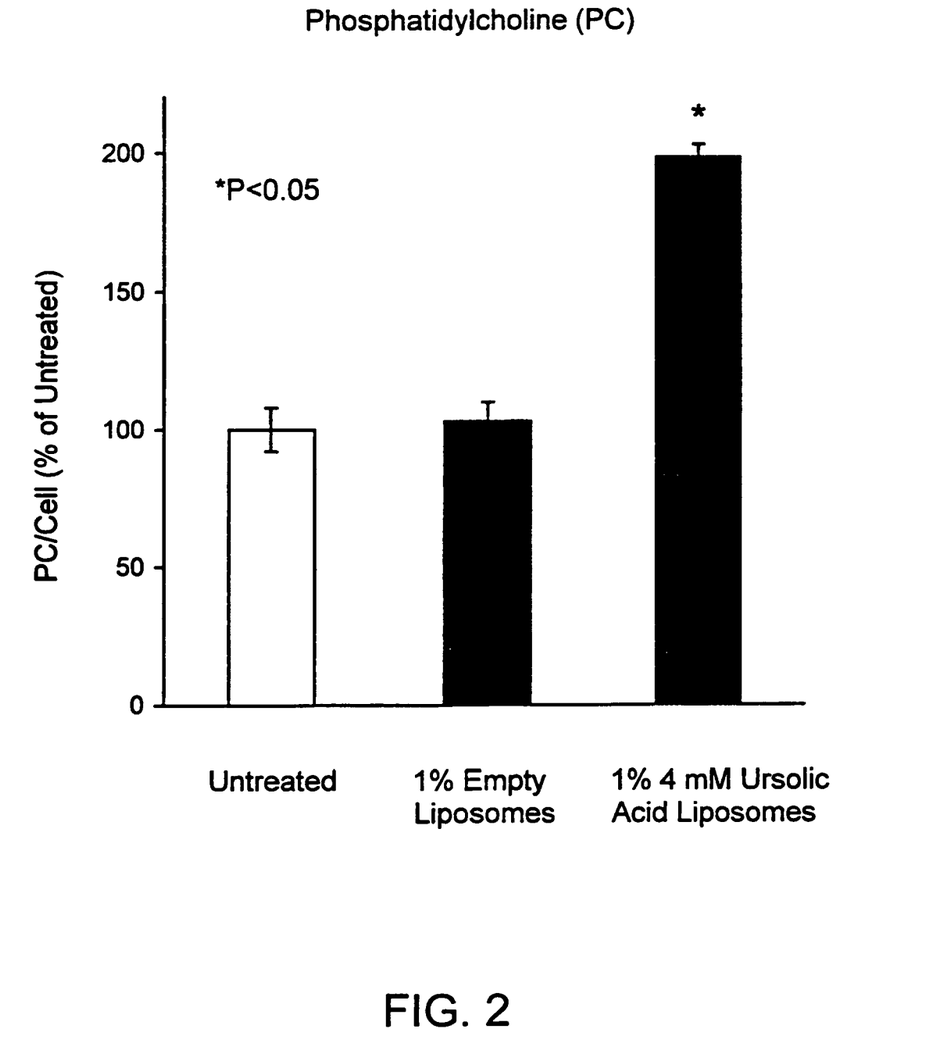
FIG. 2 shows the amount of phosphatidylcholine per cell relative to Untreated cultured normal human epidermal keratinocytes (NHEK), cultured NHEK treated with 1% (volume/volume) Empty Liposomes, or cultured NHEK treated with 1% 4 mM Ursolic Acid Liposomes. Details are described in Example 1.
Figure 3:
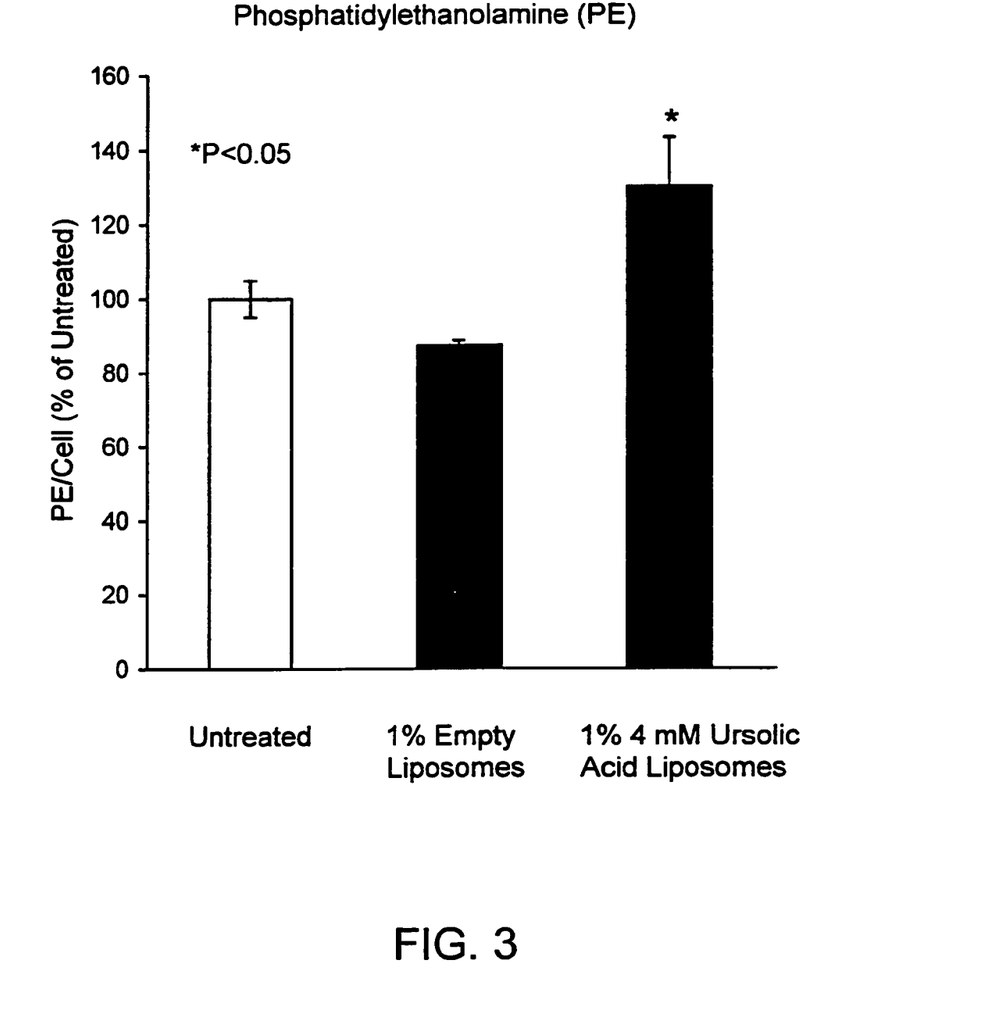
FIG. 3 shows the amount of phosphatidylethanolamine per cell relative to Untreated cultured normal human epidermal keratinocytes (NHEK), cultured NHEK treated with 1% (volume/volume) Empty Liposomes, or cultured NHEK treated with 1% 4 mM Ursolic Acid Liposomes. Details are described in Example 1.
Figure 4:
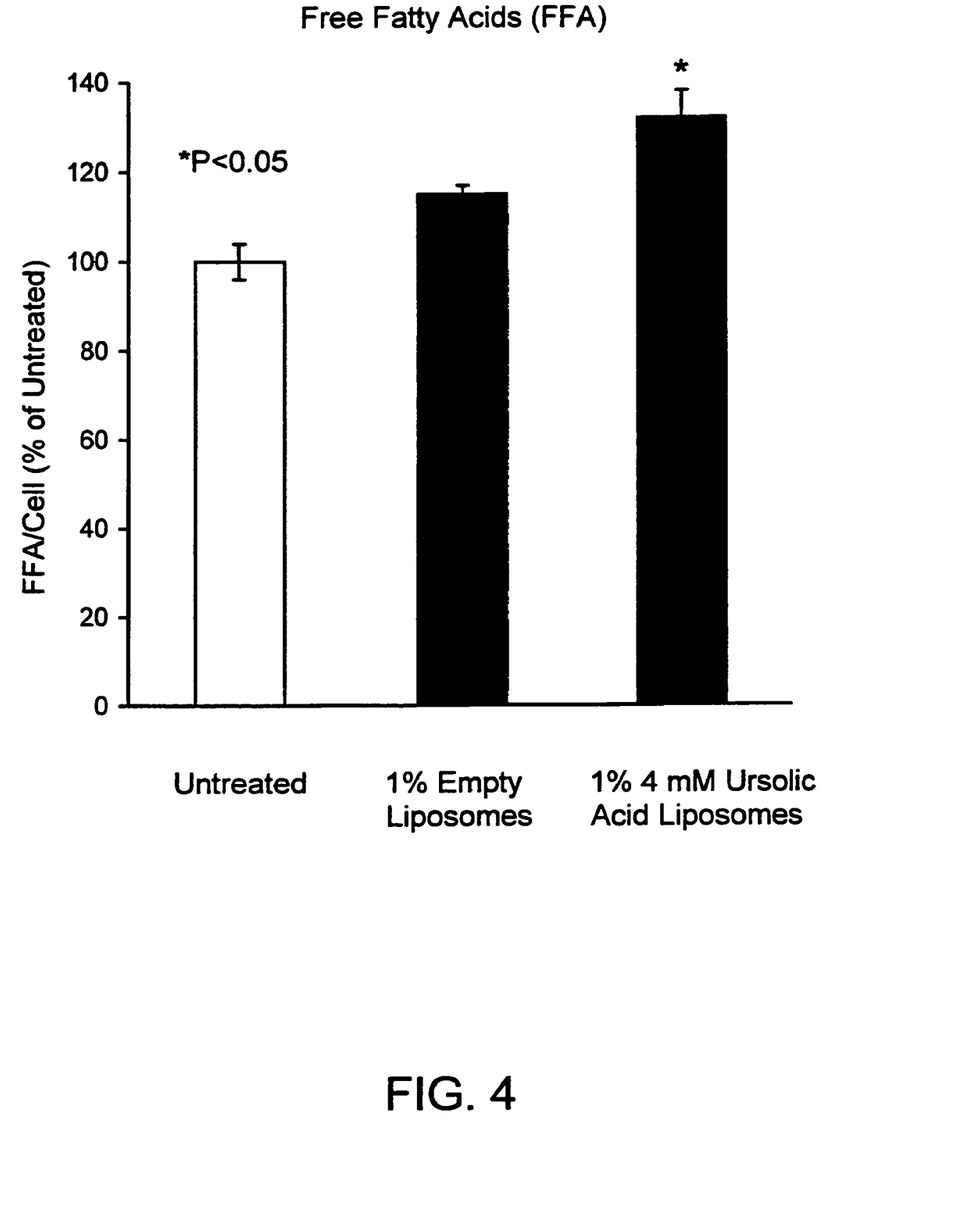
FIG. 4 shows the amount of free fatty acid per cell relative to Untreated cultured normal human epidermal keratinocytes (NHEK), cultured NHEK treated with 1% (volume/volume) Empty Liposomes, or cultured NHEK treated with 1% 4 mM Ursolic Acid Liposomes. Details are described in Example 1.
Figure 5:
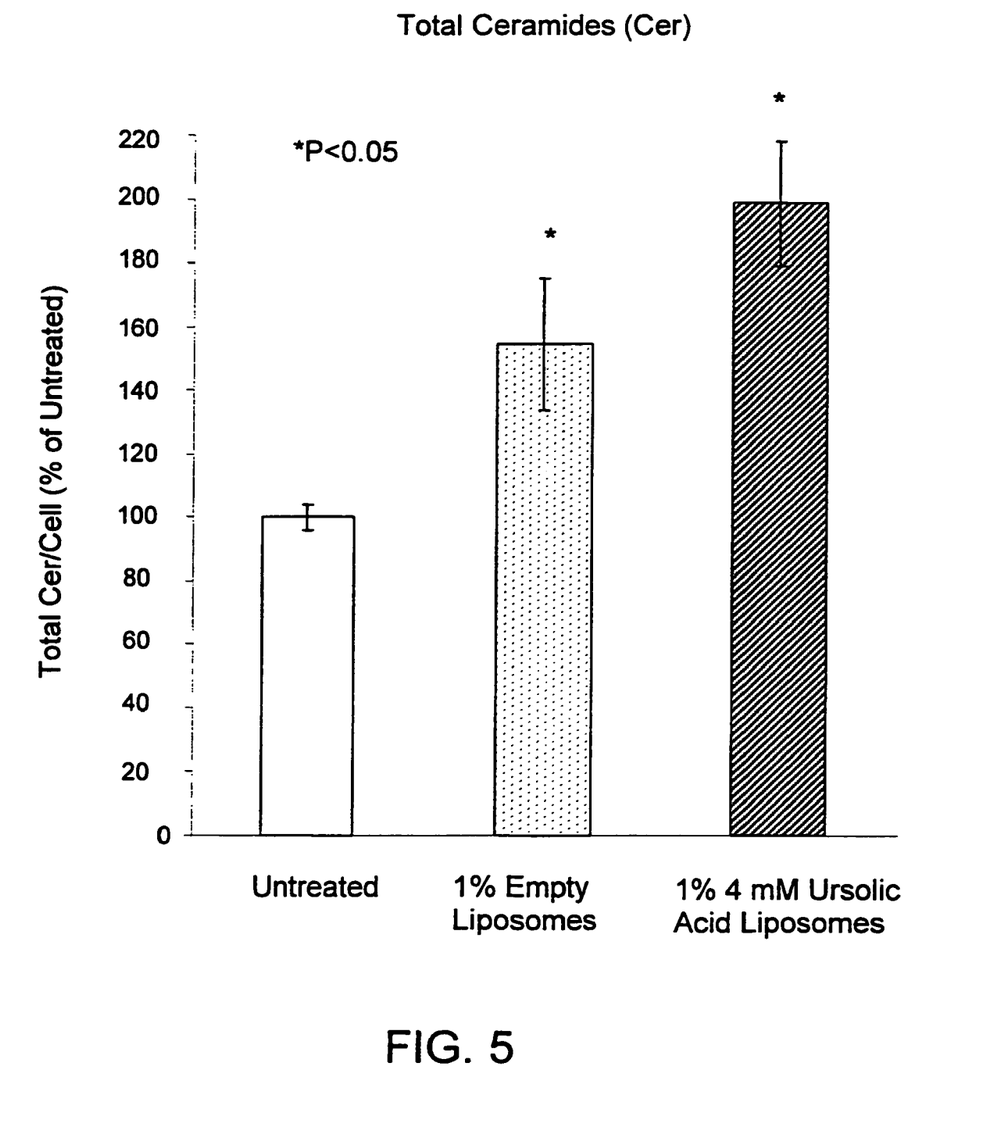
FIG. 5 shows the amount of total ceramides per cell relative to Untreated cultured normal human epidermal keratinocytes (NHEK), cultured NHEK treated with 1% (volume/volume) Empty Liposomes, or cultured NHEK treated with 1% 4 mM Ursolic Acid Liposomes. Details are described in Example 1
Figure 6:
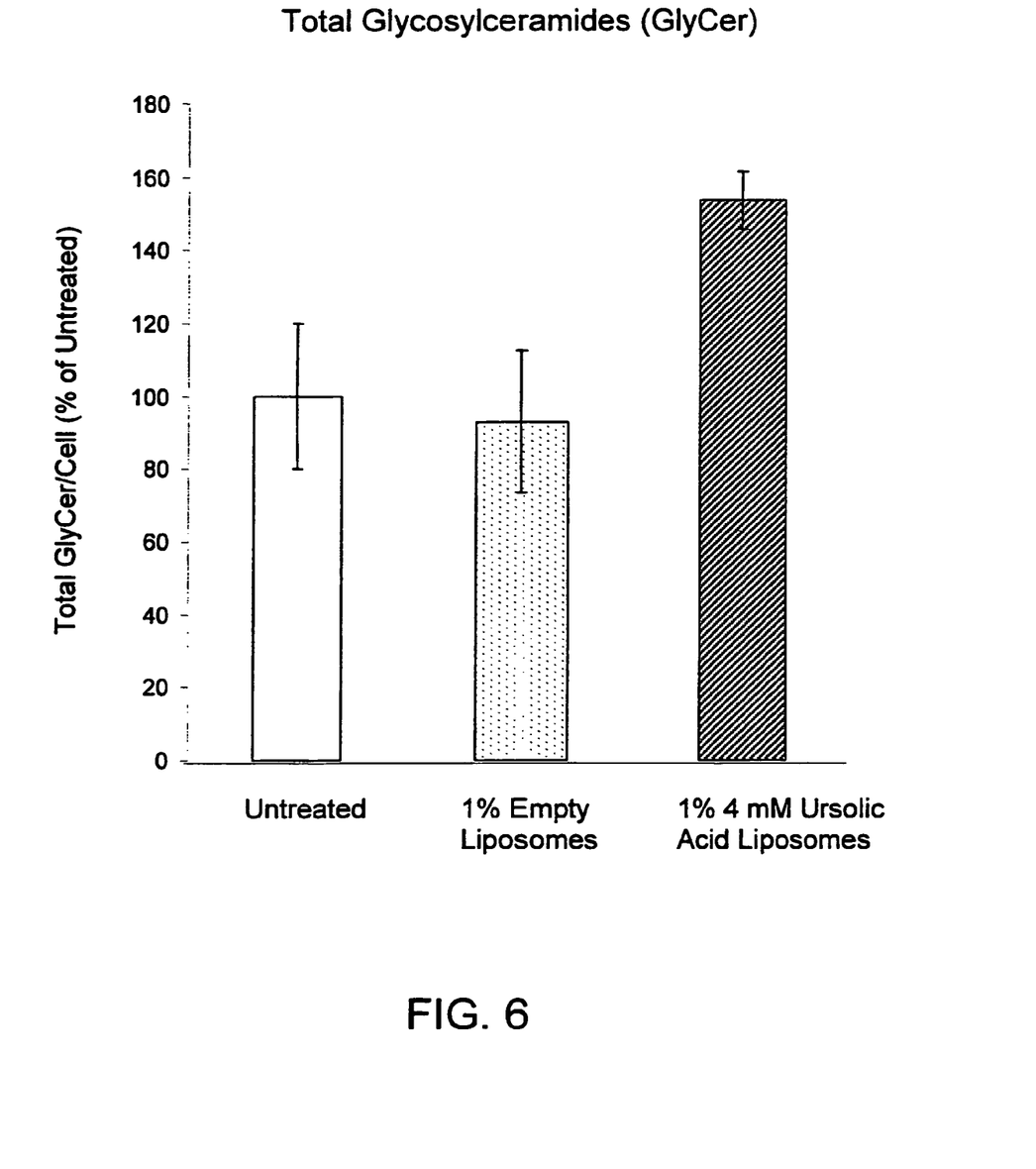
FIG. 6 shows the amount of total glycosylceramides per cell relative to Untreated cultured normal human epidermal keratinocytes (NHEK), cultured NHEK treated with 1% (volume/volume) Empty Liposomes, or cultured NHEK treated with 1% 4 mM Ursolic Acid Liposomes. Details are described in Example 1.
Figure 7:
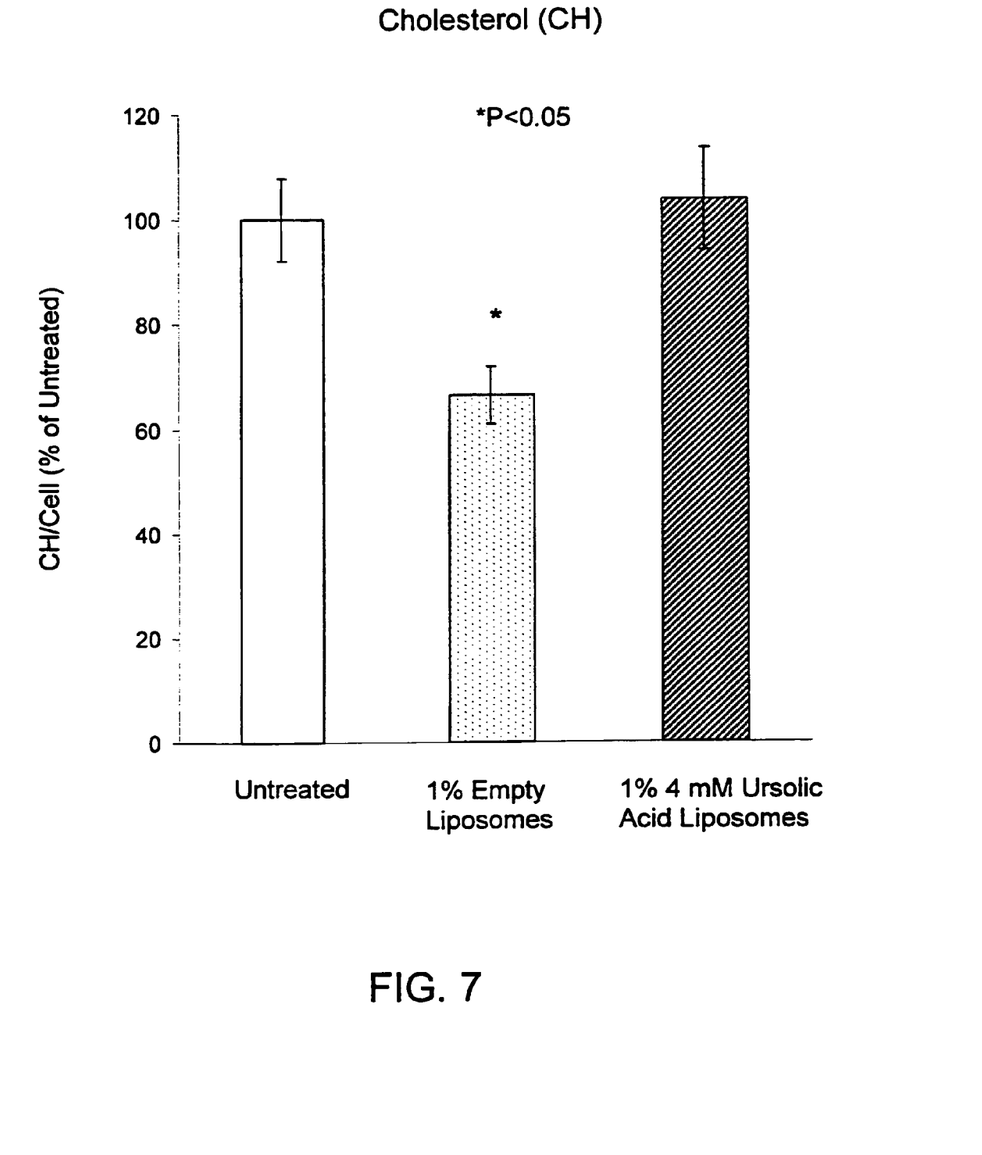
FIG. 7 shows the amount of cholesterol per cell relative to Untreated cultured normal human epidermal keratinocytes (NHEK), cultured NHEK treated with 1% (volume/volume) Empty Liposomes, or cultured NHEK treated with 1% 4 mM Ursolic Acid Liposomes. Details are described in Example 1.

Analysis of lipid content by TLC and HPTLC indicated that Ursolic Acid Liposomes resulted in a statistically significant 2-fold increase of phosphatidylcholine (PC) in NHEK relative to Untreated NHEK (FIG. 2). There was no increase of PC in NHEK treated with Empty Liposomes despite the fact that these liposomes contain PC. There was a statistically significant 1.3-fold increase of phosphatidylethanolamine (PE) in NHEK treated with Ursolic Acid Liposomes (FIG. 3). Treatment of NHEK with Empty Liposomes resulted in a 13% decrease of PE, although this was not statistically significant. Empty liposomes resulted in a 1.15-fold increase of free fatty acids (FFA) while Ursolic Acid Liposomes resulted in 1.3-fold increases of FFA; only the increase of FFA induced by Ursolic Acid Liposomes was statistically significant (FIG. 4). Ursolic acid liposomes dramatically increased total ceramides and glycosylceramides compared to untreated cells (FIGS. 5 and 6). Neither Empty Liposomes nor Ursolic Acid Liposomes increased cholesterol levels in cells (FIG. 7). These findings in keratinocytes are unexpected in view of the reports in the prior art that ursolic acid reduces cholesterol levels and is hypolipidemic.

Figure 8:
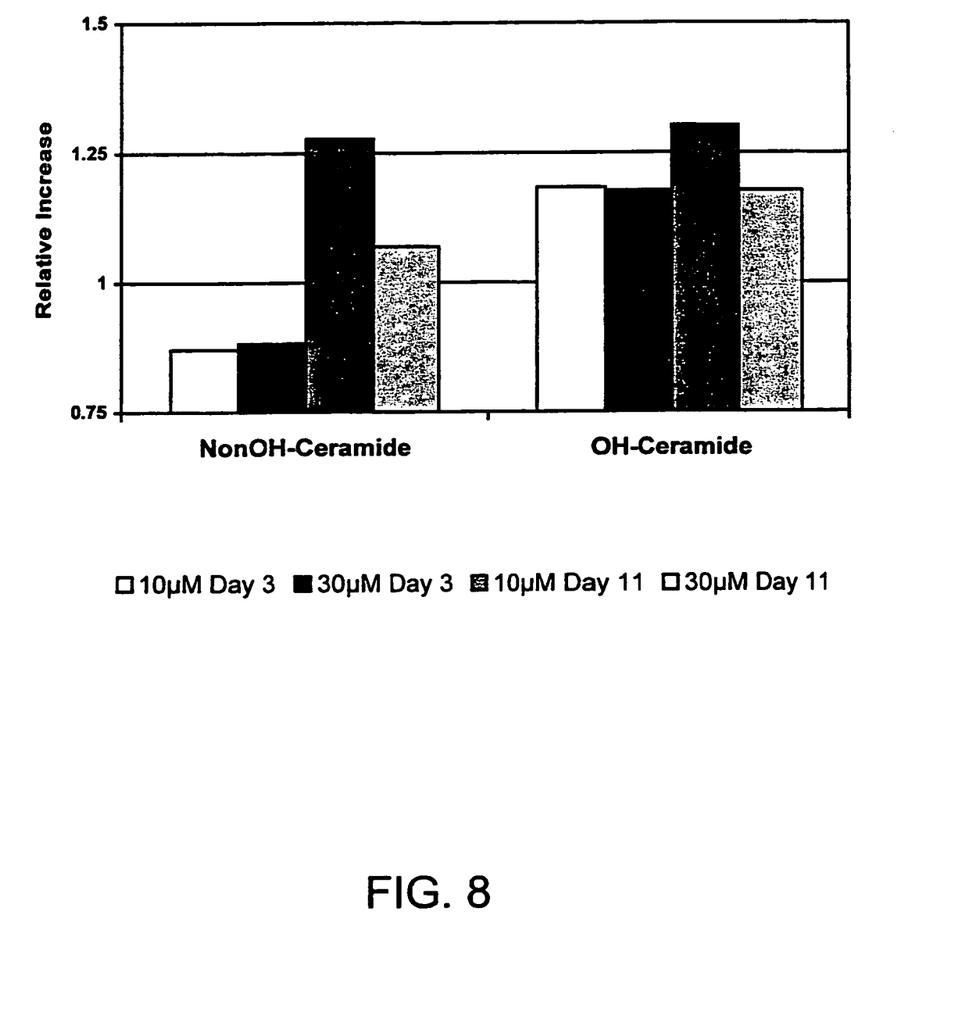
FIG. 8 shows the amount of extractable ceramides in human skin following treatment with 0.3% or 1% Ursolic Acid Liposomes in a hydrogel Lotion for 3 and 11 days, relative to adjacent areas treated with Empty Liposome Lotion. These concentrations of Ursolic Acid Liposomes resulted in a final concentration of ursolic acid in the hydrogel Lotion of 10 $\mu$M and 30 $\mu$M, respectively.

Treatment of human subjects with lotion containing 10 $\mu$M or 30 $\mu$M liposomal ursolic acid resulted in induction of ceramides, with increases of hydroxy-ceramides generally greater than non-hydroxy-ceramides (FIG. 8). In fact, following 3 days of treatment, non-hydroxy ceramides were decreased approximately 12% by 10 $\mu$M or 30 $\mu$M liposomal ursolic acid. In contrast, hydroxy ceramides were increased by approximately 18% following 3 days of treatment with either 10 $\mu$M or 30 $\mu$M liposomal ursolic acid. Following 11 days of treatment, both non-hydroxy and hydroxy ceramides were increased approximately 30% by 10 $\mu$M liposomal ursolic acid. However, at this same time period, non-hydroxy and hydroxy ceramides were increased only 7% and 18% respectively, by 30 $\mu$M ursolic acid. Thus, whereas 30 $\mu$M liposomal ursolic acid was a more optimal concentration for induction of ceramides in cultured NHEK, 10 $\mu$M liposomal ursolic acid was a more optimal concentration for induction of ceramides in human skin. However, it should be noted that whereas cell culture treatments were done only once every third day, treatment of human skin was done twice daily. Thus, the ability of liposomal ursolic acid to induce ceramides in human skin may have been saturated by this treatment regimen.

Previous studies have shown that alterations of specific lipids can be associated with functional and aesthetic changes in skin. For example, treatment of skin with retinoids results in increases of phospholipids, a reduction of ceramides, and reduced senescence of epidermal cells. Thus, the viability and vitality of skin is increased while the barrier function is reduced. Furthermore, it is known that lipid accumulation in epidermal cells is associated with a restoration of a youthful appearance.

Similar to retinoids, the compounds of the present invention result in increased levels of phospholipids in cells. However, incorporation of the compounds of the present invention into liposomes results in accumulation of additional lipids, including total ceramides and glycosylceramides which are extremely important for barrier function. Thus, unlike results with retinoids wherein ceramide levels are decreased (Ponec and Weerheim, 1990, Meth. Enzymol. 190:31–40), the barrier function of skin will not be compromised by the compositions of the present invention. In addition, the compositions will stimulate phospholipid synthesis and thereby increase cell viability. Thus, the topical administration of a ursolic acid compound in accordance with the invention will serve to counteract the effects of aging and photoaging and to treat diseases of dry skin related to impaired barrier function and dysfunctional stratum corneum.

TABLE I

| Name | $R_1$ | $R_2$ | $R_3$ | $R_4$ | $R_5$ | $R_6$ | $R_7$ | $R_8$ | X | Ring E |
|---|---|---|---|---|---|---|---|---|---|---|
| Ursolic acid | H | OH | $CH_3$ | H | COOH | H | H | $CH_3$ | -ene | hexyl |
| Oleanolic acid | | | | | | $CH_3$ | | H | | |
| Erythrodiol | | | | | $CH_2OH$ | $CH_3$ | | H | | |
| 12,13-epoxyoleanolic acid | | | | | | $CH_3$ | | H | -epoxy | |
| Uvaol | | | | | $CH_2OH$ | | | | | |
| Hederagenin | | | $CH_2OH$ | | | $CH_3$ | | | | |
| Corosolic acid | OH | | | | | | | | | |
| Euscapic acid | OH | | | | | | OH | | | |
| 18β-glycyrrhetic acid | | | | O= | $CH_3$ | COOH | | H | | |
| Carbenoxolone | | $CO(CH_2)_2$—$CO_2H$ | | O= | | COOH | | H | | |
| Glycyrrhetol | | | | O= | $CH_3$ | $CH_2OH$ | | | | |
| Betulin | | | | | | $CH_2OH$ | COOH | H | | Pentyl |
| Betulinic acid | | | | | | | COOH | H | | Pentyl |
| Lupane | | | | | | $CH_3$ | $COCH_2OH$ | H | | Pentyl |
| New Lupane | | | | | | $CH_2OH$ | COCHO | H | | Pentyl |

Ursolic acid is the reference compound. Blank cells indicate that the site is identical to ursolic acid.

What is claimed is:

1. A method for increasing the lipid content of the epidermal keratinocytes of the skin of a mammal in need of said increase comprising topically administering a ursolic acid compound encapsulated in liposomes to said skin in an amount effective to increase the lipid content of said epidermal keratinocytes, said liposomes comprising phospholipid bilayer membranes, wherein said increase in lipid content comprises an increase in at least one member of the ceramide lipid family.

2. The method of claim 1 wherein (i) the skin of the mammal is skin that exhibits aging as a result of a reduction in the lipid content of its epidermal layer and (ii) the ursolic acid compound is topically administered to said skin in an amount effective to reduce the effects of aging exhibited by said skin.

3. The method of claim 1 wherein (i) the skin of the mammal is skin that exhibits photoaging as a result of a reduction in the lipid content of its epidermal layer and (ii) the ursolic acid compound is topically administered to said skin in an amount effective to reduce the effects of photoaging exhibited by said skin.

4. The method of claim 1 wherein (i) the skin of the mammal is skin that has atrophied as a result of a reduction in the lipid content of its epidermal layer and (ii) the ursolic acid compound is topically administered to said skin in an amount effective to reduce the atrophy of said skin.

5. The method of claim 4 wherein the reduction in the lipid content of the epidermal layer is a result of the application of at least one retinoid to the skin.

6. The method of claim 4 wherein the reduction in the lipid content of the epidermal layer is a result of the application of at least one steroid to the skin.

7. The method of claim 1 wherein (i) the skin of the mammal suffers from ichthyosis or ichthyosiform dermatoses and (ii) the ursolic acid compound is topically administered to said skin in an amount effective to reduce said ichthyosis or ichthyosiform dermatoses.

8. The method of claim 1 wherein (i) the mammal has the sensation of dry skin as a result of a reduction in the lipid content of the skin's epidermal layer and (ii) the ursolic acid compound is topically administered to the skin of said mammal in an amount effective to reduce said sensation of dry skin.

9. The method of claim 1 wherein the ursolic acid compound is administered in a formulation and the concentration of the ursolic acid compound in that formulation is equal to or less than 30 micromolar.

10. The method of claim 1 wherein the ursolic acid compound is administered in a preparation comprising a water soluble preservative.

11. The method of claim 10 wherein the water soluble preservative is potassium sorbate.

12. The method of claim 1 wherein the ursolic acid compound is ursolic acid.

13. The method of claim 1 wherein the content of free fatty acids is increased.

14. The method of claim 1 wherein the ursolic acid compound is administered in combination with at least one other active compound which is not a ursolic acid compound.

15. The method of claim 14 wherein the at least one other active compound is a retinoid.

16. The method of claim 14 wherein the at least one other active compound is a steroid.

17. The method of claim 1 wherein the mammal is a human.

\* \* \* \* \*